United States Patent
Hoffman

(10) Patent No.: US 7,730,628 B2
(45) Date of Patent: Jun. 8, 2010

(54) DEPTH STOP DEVICES AND SYSTEMS

(75) Inventor: Raymond C. Hoffman, Gibsonia, PA (US)

(73) Assignee: Bayer Schering Pharma AG, Berlin (DE)

( * ) Notice: Subject to any disclaimer, the term of this patent is extended or adjusted under 35 U.S.C. 154(b) by 55 days.

(21) Appl. No.: 12/204,887

(22) Filed: Sep. 5, 2008

(65) Prior Publication Data
US 2010/0058603 A1 Mar. 11, 2010

(51) Int. Cl.
*G01B 21/18* (2006.01)
(52) U.S. Cl. .......................................... 33/512; 33/836
(58) Field of Classification Search .................. 33/512, 33/836
See application file for complete search history.

(56) References Cited

U.S. PATENT DOCUMENTS

| | | | | |
|---|---|---|---|---|
| 1,436,707 | A | * | 11/1922 | Gaschke .................... 604/117 |
| 4,039,266 | A | * | 8/1977 | O'Connell .................. 408/202 |
| 4,710,075 | A | * | 12/1987 | Davison ..................... 408/202 |
| 4,710,171 | A | | 12/1987 | Rosenberg |
| 4,787,794 | A | * | 11/1988 | Guthrie ....................... 411/433 |
| 4,992,010 | A | * | 2/1991 | Fischer ....................... 408/159 |
| 5,147,164 | A | * | 9/1992 | Fraver ........................ 408/202 |
| 5,217,438 | A | | 6/1993 | Davis |
| 6,612,990 | B1 | | 9/2003 | Pruter |
| 6,694,832 | B1 | * | 2/2004 | Gleeson ..................... 73/866.5 |
| 6,789,986 | B2 | * | 9/2004 | Story, Jr. .................... 409/218 |
| 7,485,113 | B2 | * | 2/2009 | Varner et al. ................ 604/521 |
| 7,507,210 | B2 | * | 3/2009 | Hibner et al. ............... 600/567 |
| 7,513,722 | B2 | * | 4/2009 | Greenberg et al. .......... 408/202 |

FOREIGN PATENT DOCUMENTS

WO WO2007053779 5/2007

OTHER PUBLICATIONS

CRW (Radionics) Disposable Depth Stops Product No. DS11, DS16, DS18, DS21, DS25 and DS30, CRW Catalog Product Sheet, 2006.
Vlier Mechanical Components—Torque Thumb Screws, Product Data Sheet, Vlier website (www.vlier.com).
Vlier Standard Plungers—Steel & Stainless Steel, Product Data Sheet, Vlier website (www.vlier.com).
Popper Vomed Special Needles/Trocars with Trumpetvalve, Product Data Sheet, Popper & Sons, Inc. (Undated).
Popper Adapters and Tubing Connectors, Product Data Sheet, Popper & Sons, Inc. (Undated).

* cited by examiner

*Primary Examiner*—Christopher W Fulton
(74) *Attorney, Agent, or Firm*—Gregory L. Bradley; Henry E. Bartony, Jr.

(57) ABSTRACT

A depth stop device for use in connection with another device or apparatus (for example, a medical device) includes a stop member slidably positionable on the device, at least one abutment member in operative connection with the stop member to adjustably contact the device to lock the stop member in a desired position relative to the device or to free the stop member to slide relative to the device, and an adjustment member connected to the abutment member to control a position of the abutment member relative to the device. The force applicable by the abutment member to the device is limited to be less than a certain force.

6 Claims, 3 Drawing Sheets

DEPTH STOP DEVICES AND SYSTEMS

BACKGROUND OF THE INVENTION

The present invention relates to depth stop devices and systems and, particularly, to depth stop devices and systems for use in connection with, for example, medical devices such as biopsy instruments, needles or cannulae to control, for example, position, extension, placement and/or penetration.

The following information is provided to assist the reader to understand the invention disclosed below and the environment in which it will typically be used. The terms used herein are not intended to be limited to any particular narrow interpretation unless clearly stated otherwise in this document. References set forth herein may facilitate understanding of the present invention or the background of the present invention. The disclosure of all references cited herein are incorporated by reference.

In many medical depth stop devices such as needle depth stop devices and systems (sometimes referred to simply as depth stops) currently in use, a bushing or stop member slides over a medical device (for example, via which fluid is injected into and/or fluid/tissue is withdrawn from the body) and is clamped or locked in place on the medical device via a set screw. The depth stop device can, for example, abut a surface of instrumentation or tissue (such as skin) to, for example, limit the depth to which a penetrating medical device can be inserted. The set screw include a gripping member such as a knurled knob for tightening the screw against, for example, a biopsy needle, a fluid injection needle or a cannula by hand. Such knobs typically have a small diameter to limit the torque that can be applied to the screw. In that regard, excessive torque can damage medical devices such as needles or cannulae, which typically have relatively thin walls. However, limiting applied torque by limiting the size or diameter of a gripping member results in difficulty in operating the depth stop device, particularly in the case of a physician wearing sterile gloves.

It is desirable to develop improved depth stop devices and systems that reduce or eliminate the above-identified and/or other problems associated with currently available depth stop devices and systems.

SUMMARY OF THE INVENTION

In one aspect, the present invention provides a depth stop device for use in connection with another device or apparatus. The depth stop device includes a stop member slidably positionable on the device, at least one abutment member in operative connection with the stop member to adjustably contact the device to lock the stop member in a desired position relative to the device or to free the stop member to slide relative to the device, and an adjustment member connected to the abutment member to control a position of the abutment member relative to the device. The force applicable by the abutment member to the device is limited to be less than a certain force.

The adjustment member can, for example, include a threaded member that is movable to adjust the position of the abutment member. The abutment member can, for example, include a surface of the depth stop member that is movable upon rotation of the threaded member.

The depth stop surface can, for example, be at least a portion of a surface of a passage formed in the stop member through which the device can be passed. The passage can be in communicative connection with a slot formed in the stop member. The width of the slot can be adjustable via rotation of the threaded member to adjust the force applicable by at least a portion of the surface of the passage to the device.

The portion of the surface of the passage can, for example, be formed on a cantilever arm of the depth stop. In this embodiment, the threaded member can be rotatable to abut and move the cantilever arm.

In a number of embodiments, the slot extends from the passage, dividing the depth stop member into two sections. The threaded member can, for example, be in threaded connection with at least one of the sections such that rotation of the threaded member adjusts the width of the slot.

In several other embodiments, the abutment member is slidably positioned within a passage in the threaded member. The threaded member can, for example, further include a biasing element within the passage in contact with the abutment member. The biasing element limits the force applicable by the abutment member to the device. The biasing element can, for example, include a compressible member. The distance the threaded member can slide within the passage can be limited to limit the compression of the compressible member, thereby limiting the force applicable by the abutment member. In several embodiments, the compressible member comprises a spring.

The depth stop device can further include a gripping member connected to the threaded member, wherein the gripping member has a diameter greater than the threaded member. In several embodiments, the gripping member is a knob having a diameter of at least ¼ inch.

In another aspect, the present invention provides a system including a medical device and a depth stop device for use in connection with the medical device as described above. In that regard, the depth stop device includes a stop member slidably positionable on the medical device, at least one abutment member in operative connection with the stop member to adjustably contact the medical device to lock the stop member in a desired position relative to the medical device or to free the stop member to slide relative to the device, and an adjustment member connected to the abutment member to control a position of the abutment member relative to the medical device. The force applicable by the abutment member to the medical device is limited to be less than a certain force. In several embodiments, the medical device is a needle or a cannula.

The present invention, along with the attributes and attendant advantages thereof, will best be appreciated and understood in view of the following detailed description taken in conjunction with the accompanying drawings.

DETAILED DESCRIPTION OF THE INVENTION

As used herein and in the appended claims, the singular forms "a," "an", and "the" include plural references unless the content clearly dictates otherwise. Thus, for example, reference to "a stop member" includes a plurality of such stop members and equivalents thereof known to those skilled in the art, and so forth, and reference to "the stop member" is a reference to one or more such stop members and equivalents thereof known to those skilled in the art, and so forth.

Figure 1:
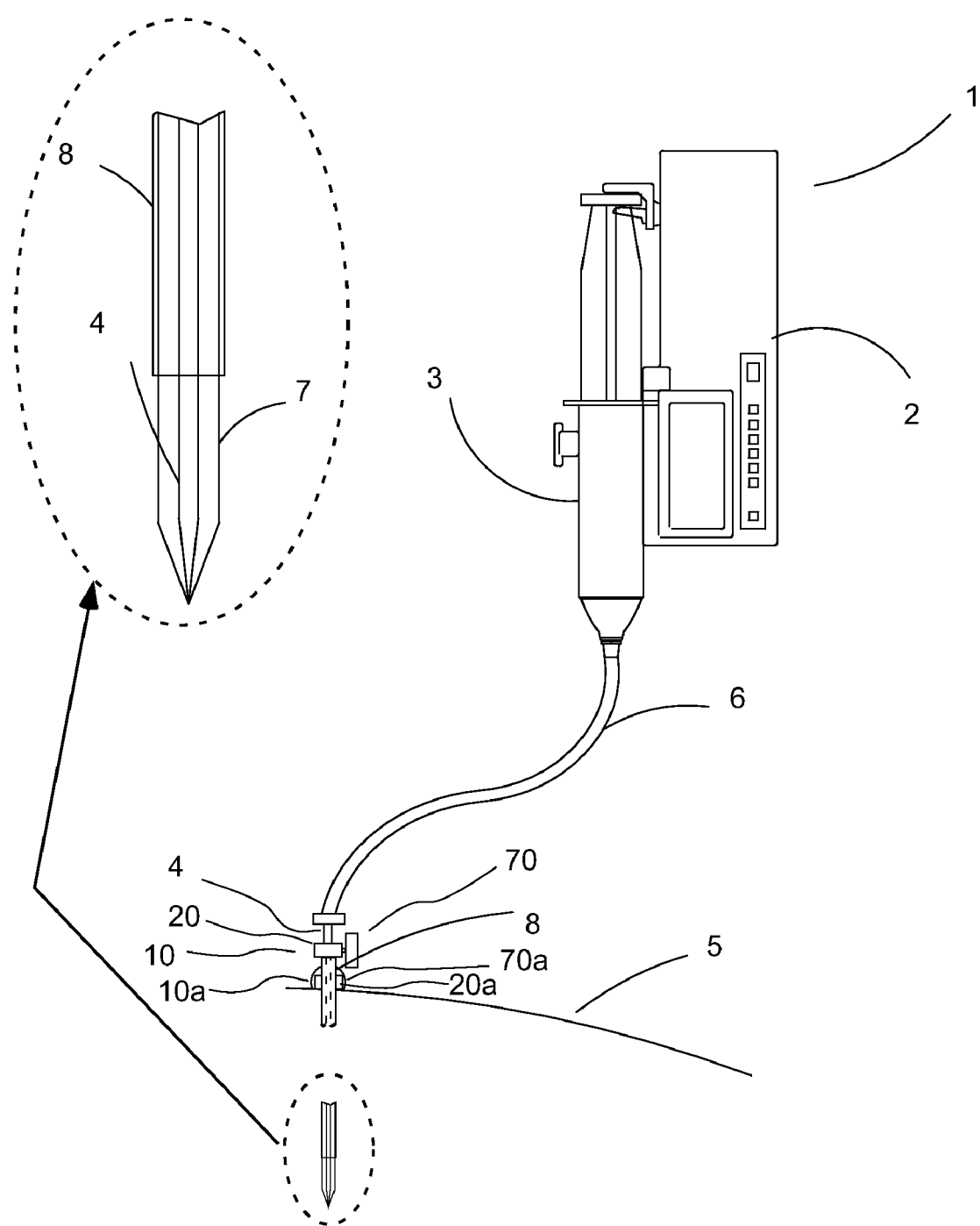
FIG. 1 illustrates an embodiment of an injection system in which an embodiment of a depth stop device of the present invention is used in connection with a needle passing through a cannula as well as in connection with the cannula.

FIG. 1 illustrates use of a representative example of depth stop device or systems 10 and 10a of the present invention in connection with an embodiment of a pump/injector system 1 for use in injection of, for example, a Parkinson's disease treatment/drug into the brain of a patient. In the illustrated embodiment, injector system 1 includes a syringe pump 2 to deliver the drug from a syringe 3 to the patient. Syringe 3 can, for example, be placed in fluid connection with a needle 4 localized by a stereotactic frame or similar localization device 5 via a length of flexible tubing 6. Further, needle 4 can pass through a cannula 8 in operative connection with stereotactic frame 5. Connection of syringe pump system 2 to needle 4 via flexible tubing 6 can operate to isolate needle 4 and stereotactic frame 5 from force, torque, or vibration as, for example, disclosed in Published PCT International Patent Application No. WO/2007/053779, the disclosure of which is incorporated herein by reference. Alternatively, needle 4 can, for example, be directly connected to a manual syringe for manual delivery of the drug therefrom.

In the system illustrated in FIG. 1, first depth stop device 10 is fixed to needle 4 and abuts an upper surface of cannula 8 to control the position of needle 4 relative to cannula 8 and thereby the depth of penetration of needle 4. A second depth stop device 10a is fixed to cannula 8 and abuts an upper surface of stereotactic frame 5 to position cannula 8 with respect to stereotactic frame, providing further control of the depth of penetration of needle 4. The positions of depth stop devices 10 and/or 10a can be changed during a procedure to enable injection at two or more desired depths/positions. Depth stop devices 10 and 10a can, for example, be essentially identical in form and function, with depth stop 10a having a larger passage to accommodate the larger diameter of cannula 8 as compared to needle 4.

As described above, depth stop devices of the present invention are usable in connection with medical or other devices to control position, extension, placement and/or penetration. In general, the depth stop devices of the present invention include an adjustable stop member or bushing that is slidably positionable on the device. The depth stop devices of the present invention also include at least one abutment member in operative connection with the stop member to adjustably contact the device to clamp or lock the stop member in a desired position relative to the device or to release the stop member to move/slide relative to the device. An adjustment member is operatively connected to the abutment member to control the position of the abutment member relative to the device. The force applicable by the abutment member to the device is limited to be less than a certain force so that substantially no damage will be caused to the device.

Figure 2:
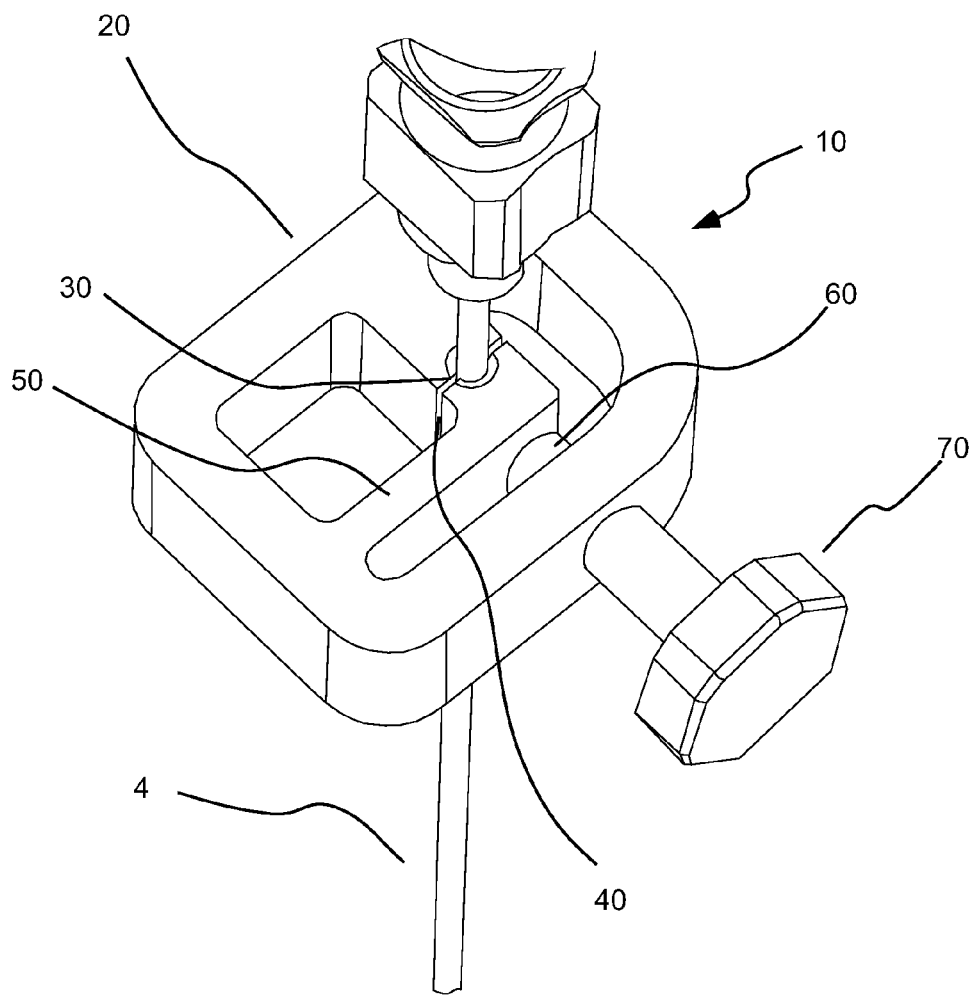
FIG. 2 illustrates a top view of the depth stop device of FIG. 1.

FIG. 2 illustrates an enlarged perspective view of depth stop device 10. A main body or stop member 20 of depth stop device 10 has a pilot hole or passage 30 formed (for example, drilled) therein which can, for example, be smaller than the outside diameter of an extending device such as needle 4 or a cannula. In the illustrated embodiment, narrow slot 40 is formed (for example, machined) through stop member 20 which bisects passage 30. One half of passage 30 is generally rigidly mounted to stop member 20. The other half of passage 30 (as a result of formation of slot 40) is connected to an extending cantilever arm 50. Cantilever arm 50 can be deflected, via an adjusting member 60 to decrease the width of slot 40 or even close slot 40 completely. With slot 40 in a narrow state or in a fully closed state, the portion of the surface of passage 30 on cantilever arm 50 abuts needle 4. Passage 30 can be sized to a desired interference fit with needle 4, wherein the surfaces forming passage 30 exert sufficient force upon needle 4 to hold depth stop device 10 at a desired position on needle 4. Allowing cantilever arm 50 to relax (for example, via adjusting member 60), results in widening of slot 40 so that passage 30 exerts less force on needle 4 or becomes larger than needle 4 and exerts no force on needle 4, thereby permitting depth stop device 10 to slide easily up or down needle 4. Deflecting the cantilever arm 50 toward needle 4 decreases the width of slot 40 and reduces the diameter of passage 30 generally uniformly around needle 4, locking or clamping the depth stop device 10 in place. Various adjustment methods or devices can be used to deflect the cantilever arm 50. In the illustrated embodiment, a knurled knob 70 is used to tighten or loosen an adjustment member in the form of a threaded shaft 60 which abuts cantilever arm 50 to controllably adjust the position of or deflection of cantilever arm 50.

In depth stop device 10, the force exerted upon needle 4 is limited to be less than a certain predetermined force (for example, 8 to 10 pounds), which is chosen to adequately lock depth stop device 10 in a desire position on needle 4 while preventing substantial (or any) damage to needle 4. In that regard, once passage 30 is fully closed, further movement/rotation of adjustment member 60 will not increase the force exerted upon or applied to needle 4. Stop member 20 can, for example, be formed form a metallic material such as aluminum etc. or from a resilient polymeric material such as polycarbonate, polypropylene, acrylonitrile butadiene styrene (ABS), etc. The design of depth stop device 10 can, for example, eliminate the need for small diameter gripping members or knobs associated with currently available depth stop devices, and further provides a more uniform clamping force about the circumference of needle 4 than provided by currently available depth stop devices. Relatively large knob 70 significantly facilitates the adjustment of depth stop device 10 as compared to currently available depth stop devices. Knobs or adjustment members used in connection with all embodiments of the depth stop devices and systems of the present invention can generally be of any size, but are preferably at least ¼ inch, at least 5/16 inch, at least ⅜ inch or even larger in diameter. In several embodiments, knob 70 was formed from a metal such as aluminum or stainless steel.

Figure 3:
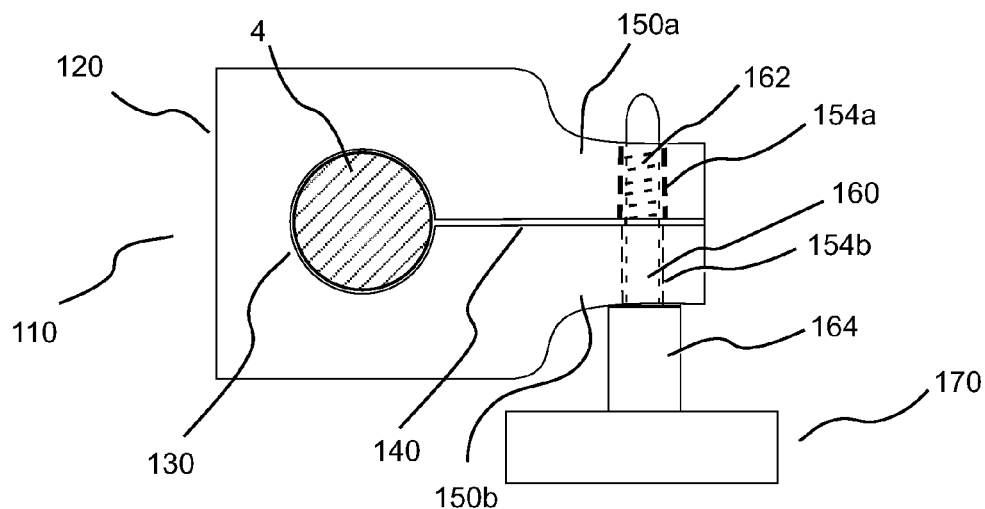
FIG. 3 illustrates a perspective view of another embodiment of a depth stop device of the present invention.

FIG. 3 illustrates another embodiment of a depth stop device 110 of the present invention which includes a stop member 120 having a passage 130 formed therethrough to slidably position stop member 120 on an extending fluid path element such as needle 4. A slot 140 is formed in one side of stop member 120 (the right side in the orientation of FIG. 3), to extend from passage 130 to the right end of stop member 120. Slot 140 divides the right side of stop member 120 into two section or arms 150a and 150b. A threaded passage 154a is formed in arm 150a of depth stop member 120 and a concentric unthreaded passage 154b is formed in arm 150b. An adjustment member in the form of a shaft 160 passing through passages 154a and 154b includes a threaded section 162, which is in threaded connection with threaded passage 154a. Rotation of shaft 160 adjusts the width of slot 140 via abutment of a shoulder 164 on shaft 162 with arm 150b.

As is the case with depth stop device 10, the force exerted upon, for example, needle 4 is limited to be less than a certain predetermined force that is chosen to prevent substantial damage or any damage to needle 4. In that regard, once passage 130 is fully closed (to a predetermined diameter), further movement/rotation of adjustment member 160 will not increase the force exerted upon or applied to needle 4. Stop member 120 can, for example, be formed form a metallic material such as aluminum etc. or a resilient polymeric material such as polycarbonate, polypropylene, acrylonitrile butadiene styrene (ABS), etc.

Figure 4:
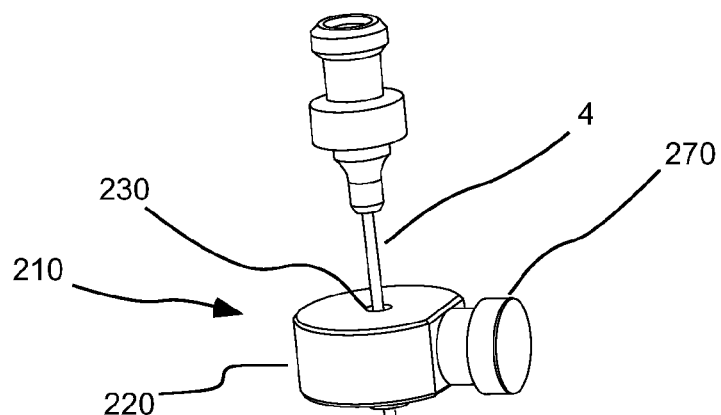
FIG. 4 illustrates a perspective view of another embodiment of a depth stop device of the present invention.
Figure 5:
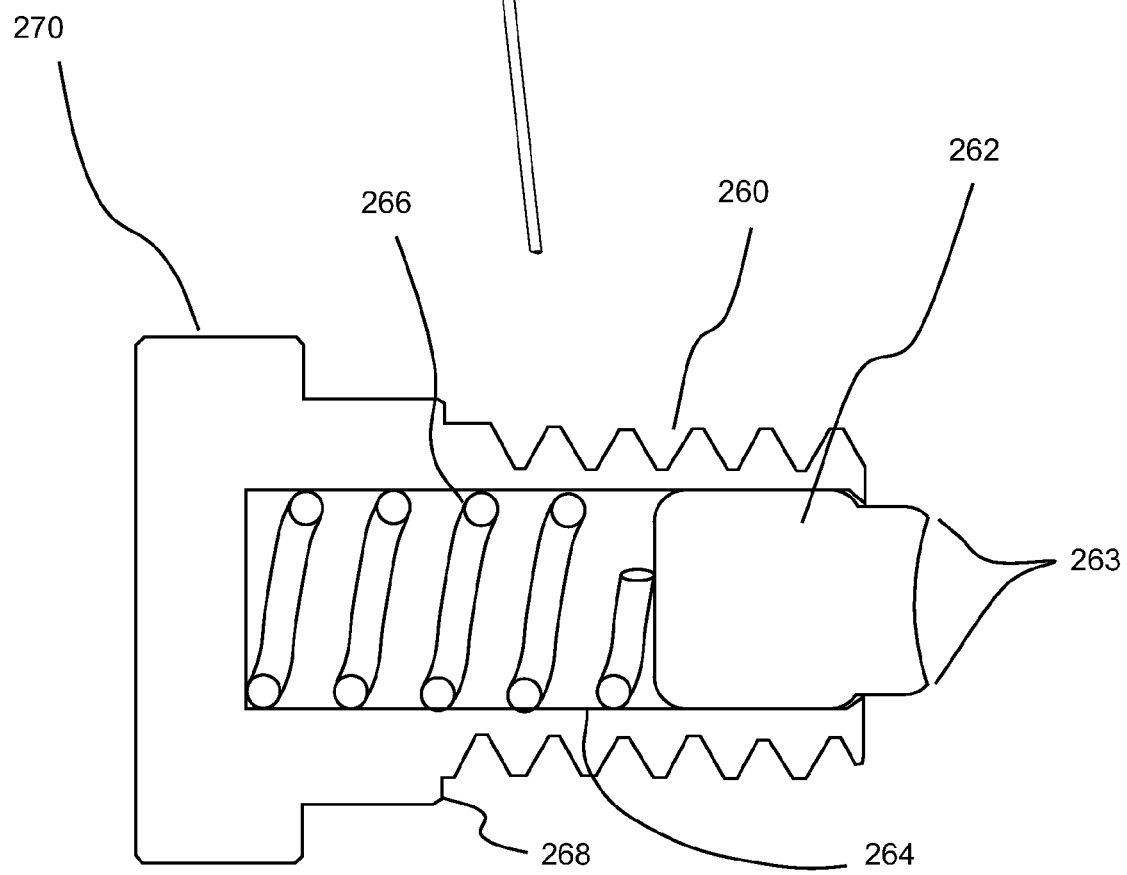
FIG. 5 illustrates a side, cutaway view of an adjustment mechanism of the depth stop device of FIG. 4.

FIGS. 4 and 5 illustrates another embodiment of force-limited needle depth stop device 210 of the present invention. A stop member or bushing 210 includes a passage 230 through which an extending medical device such as needle 4 can pass so that stop member surrounds the circumference of and is slidably positioned upon needle 4. In the illustrated embodiment, an abutment member 262 is slidably positioned within a passage 264 formed in a threaded shaft 260, which is threadably engaged within a threaded passage (not shown) formed within stop member 220 to be communication with passage 230. As shaft 260 is rotated (for example, clockwise) to advance within the threaded passage toward needle 4, a forward surface of abutment member 262 (which, in several embodiments was concave to create two peripheral contact or "biting" surfaces 263 to contact and "grip" needle 4) contacts needle 4 to exert force upon needle 4 and clamp or lock stop member 220 in position. The amount of force applied to needle 4 is limited by, for example, a compressible or otherwise deformable biasing element such as a spring 266, which is positioned within passage 264 to the rear of abutment member 262.

Spring-loaded abutment member or plunger 262 thus allows for a prescribed amount of force to be applied on needle 4 which is proportional to the spring constant of spring 266. A shoulder 268 on threaded shaft 260 can abut a surface or face stop member 220 to limit the travel of threaded member 260, preventing threaded member 260 from contacting needle 4 and preventing excessive compression of spring 266. In that regard, abutment of shoulder 268 with stop member 220 limits the amount of compression on spring 266 to a known or predetermined amount. Using the known amount of compression on spring 266 and the known spring constant of spring 266, the end force on needle 4, cannula 8 (or other device) can be determined. The end force can be varied, for example, by changing the compression on spring 266 and/or by changing the spring constant of spring 266.

The foregoing description and accompanying drawings set forth the preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A depth stop device for use in connection with a device, comprising: a stop member slidably positionable on the device, at least one abutment member in operative connection with the stop member to adjustably contact the device to lock the stop member in a desired position relative to the device or to free the stop member to slide relative to the device, and an adjustment member consisting of a threaded member that is movable to adjust the position of the abutment member, the force applicable by the abutment member to the device being limited to be less than a certain force, the abutment member also comprising a surface of the depth stop member that is movable upon rotation of the threaded member wherein the depth stop surface is at least a portion of a surface of a passage formed in the stop member through which the device can be passed, the passage being in communicative connection with a slot formed in the stop member, the width of the slot being adjustable via rotation of the threaded member to adjust the force applicable by at least a portion of the surface of the passage to the device.

2. The depth stop device of claim 1 wherein the at least a portion of the surface of the passage is formed on a cantilever arm of the depth stop, the threaded member being rotatable to abut and move the cantilever arm.

3. The depth stop device of claim 1 wherein the slot extends from the passage, dividing the depth stop member into two sections, the threaded member being in threaded connection with at least one of the sections such that rotation of the threaded member adjusts the width of the slot.

4. A system comprising a medical device and a depth stop device for use in connection with the medical device, the depth stop device comprising: a stop member slidably positionable on the medical device, at least one abutment member in operative connection with the stop member to adjustably contact the medical device to lock the stop member in a desired position relative to the medical device or to free the stop member to slide relative to the medical device, and an adjustment member consisting of a threaded member that is movable to adjust the position of the abutment member, the force applicable by the abutment member to the medical device being limited to be less than a certain force, the abutment member also comprising a surface of the depth stop member that is movable upon rotation of the threaded member wherein the depth stop surface is at least a portion of a surface of a passage formed in the stop member through which the medical device can be passed, the passage being in communicative connection with a slot formed in the stop member, the width of the slot being adjustable via rotation of the threaded member to adjust the force applicable by at least a portion of the surface of the passage to the medical device.

5. The system of claim 4 wherein the at least a portion of the surface of the passage is formed on a cantilever arm of the depth stop, the threaded member being rotatable to abut and move the cantilever arm.

6. The system of claim 4 wherein the slot extends from the passage, dividing the depth stop member into two sections, the threaded member being in threaded connection with at least one of the sections such that rotation of the threaded member adjusts the width of the slot.

* * * * *